United States Patent [19]

Smith

[11] Patent Number: 5,559,263
[45] Date of Patent: Sep. 24, 1996

[54] ALUMINUM CITRATE PREPARATIONS AND METHODS

[75] Inventor: Julie E. Smith, Lakewood, Colo.

[73] Assignee: Tiorco, Inc., Englewood, Colo.

[21] Appl. No.: 340,585

[22] Filed: Nov. 16, 1994

[51] Int. Cl.$^6$ .................................................... C07F 5/06
[52] U.S. Cl. .......................................................... 556/183
[58] Field of Search ............................................. 556/183

[56] References Cited

U.S. PATENT DOCUMENTS

| | | | |
|---|---|---|---|
| 2,327,815 | 8/1943 | Niedercorn | 260/448 |
| 3,200,136 | 8/1965 | Grossmith | 260/439 |
| 3,294,860 | 12/1966 | Loft et al. | 260/683.15 |
| 3,533,973 | 10/1970 | Stewart et al. | 260/22 |
| 3,674,726 | 7/1972 | Kirk | 260/17.4 ST |
| 3,762,476 | 10/1973 | Gall | 166/294 |
| 3,833,061 | 9/1974 | Gall | 166/294 |
| 3,839,255 | 10/1974 | Podlas | 260/29.6 M |
| 3,874,390 | 4/1975 | Eicher et al. | 131/2 |
| 3,898,186 | 8/1975 | Mermelstein et al. | 252/528 |
| 3,910,805 | 10/1975 | Catanzarite | 149/83 |
| 3,924,642 | 12/1975 | Eicher et al. | 131/2 |
| 3,952,806 | 4/1976 | Trantham | 166/294 |
| 3,964,255 | 6/1976 | Catanzarite | 60/205 |
| 3,981,363 | 9/1976 | Gall | 166/270 |
| 4,018,286 | 4/1977 | Gall et al. | 166/295 |
| 4,039,029 | 8/1977 | Gall | 166/294 |
| 4,116,931 | 9/1978 | Minhas et al. | 260/45.75 |
| 4,120,361 | 10/1978 | Threlkeld et al. | 166/294 |
| 4,274,427 | 6/1981 | Lendvay | 131/293 |
| 4,280,560 | 7/1981 | Syndansk | 166/305 R |
| 4,413,680 | 11/1983 | Sandiford et al. | 166/270 |
| 4,447,364 | 5/1984 | Staal | 260/448 R |
| 4,488,601 | 12/1984 | Hammett | 166/270 |
| 4,498,539 | 2/1285 | Bruning | 166/294 |
| 4,526,231 | 7/1985 | Radke | 166/270 |
| 4,560,783 | 12/1985 | Shioyama et al. | 556/183 |
| 4,569,393 | 2/1986 | Bruning et al. | 166/270 |
| 4,579,176 | 4/1986 | Davies et al. | 166/303 |
| 4,591,384 | 5/1986 | Akahane et al. | 106/35 |
| 4,601,340 | 7/1986 | Fodor et al. | 166/294 |
| 4,612,175 | 9/1986 | Harkness et al. | 423/235 |
| 4,645,622 | 2/1987 | Nakashima et al. | 424/52 |
| 4,657,944 | 4/1987 | Bruning et al. | 523/130 |
| 4,664,193 | 5/1987 | Wu | 166/294 |
| 4,683,949 | 8/1987 | Sydansk et al. | 166/270 |
| 4,888,136 | 12/1989 | Chellapa et al. | 252/607 |
| 4,898,842 | 2/1990 | David | 501/9 |
| 5,019,401 | 5/1991 | Drezner et al. | 424/662 |
| 5,161,615 | 11/1992 | Hutchins et al. | 166/295 |
| 5,162,378 | 11/1992 | Guthauser | 514/785 |

FOREIGN PATENT DOCUMENTS 0040763 12/1981 European Pat. Off. .
4-065802 10/1992 Japan .

OTHER PUBLICATIONS

Feng et al., "Aluminum Citrate: Isolate and Structural Characterization of a Stable Trinuclear Complex," Inorg. Chem. (1990) 29:408–411.

Gallet, J.–P. and Paris, R. A., "Etude Thermometrique de la Formation des Complexes du Fer(III), de L'Aluminium et du Gallium," Anal. Chim. Acta (1967) 39:341–348 (first page only).

Karlik, S. J. et al., "Aluminum–27 Nuclear Magnetic Resonance Study of Aluminum(III) Interactions with Carboxylate Ligands," Inorg. Chem. (1983) 22:525–529.

Lopez–Quintela, M. A. et al., "Kinetics and Thermodynamics of Complex Formation Between Aluminum(III) and Citric Acid in Aqueous Solution," J. Chem. Soc. Faraday Trans. I (1984) 80:2313–2321.

Mack, J., "Process Technology Improves Oil Recovery," Oil & Gas J. (1979) pp. 67–71.

Mak, M. K. S. and Langford, C. H., "Kinetic Analysis Applied to Aluminum Citrate Complexing," Inorg. Chim. Acta (1983) 70:237–246.

Ohman, L.–O. and Sjoberg, S., "Equilibrium and Structural Studies of Silicon(IV) and Aluminum(III) in Aqueous Solution. Part 9. A Potentiometric Study of Mono– and Poly––nuclear Aluminum(III) Citrates," J. Chem. Soc. Dalton Trans. (1983) pp. 2513–2517.

Ohman, L.–O., "Equilibrium and Structural Studies of Silicon(IV) and Aluminum(III) in Aqueous Solution. 17. Stable and Metastable Complexes in the System $H^+–AL^{3+}$–Citric Acid," Inorg. Chem. (1988) 27:2565–2570.

Parmeswar, R. and Willhite, S., "A Study of the Reduction of Brine Permeability in Berea Sandstone With the Aluminum Citrate Process," SPE Reservoir Eng. (1988) pp. 959–966.

Weise, G. and Veith, J. A., "Komplexbidung Zwischen Zitronensaure und Aluminium," Z. Naturforsch. (1975) 30b:446–453 (abstract only submitted).

Gregor, J. E. and Powell, H. K. J., "Aluminum(III)–Citrate Complexes: a Potentiometric and $^{13}C$ N.M.R. Study," Aust. J. Chem. (1986) 39:1851–1864.

*Primary Examiner*—Porfirio Nazario-Gonzales
*Attorney, Agent, or Firm*—Greenlee, Winner and Sullivan, P.C.

[57] ABSTRACT

A method for the preparation, drying and use of a stable aluminum citrate solution is disclosed. The method involves first mixing a solution containing an aluminum-chloride compound having a molar ratio of aluminum to chloride greater than about 1:3 with an aqueous solution comprising citrate. This "starter" solution is agitated at a sufficient rate to keep the slurry moving while the pH of the mixture is adjusted to a level of about 5.0 to about 9.0. The final aluminum citrate product is used to crosslink water-soluble polymer in solution for the purpose of restricting water flow in subterranean formations. The resultant aluminum citrate solution may be used either as a liquid or dried prior to shipping and using at a remote location.

11 Claims, No Drawings

ALUMINUM CITRATE PREPARATIONS AND METHODS

FIELD OF THE INVENTION

This invention provides novel aluminum citrate preparations in dry and liquid form suitable for enhancing polymer crosslinking in secondary and tertiary oil recovery.

BACKGROUND OF THE INVENTION

Aluminum citrate is useful for crosslinking polymeric materials in subterranean formations to reduce the permeability of the formations to water. In oil producing formations, aluminum citrate has been used as a crosslinker for several years to improve oil recovery beyond what is recoverable by primary methods. Primary recovery involves production of the oil from the formation by natural driving forces such as gas expansion. Primary recovery normally only produces about one-third of the oil in the reservoir, leaving two-thirds of the oil still in place in the formation. Another one-third of the oil in the formation may be recovered by secondary or tertiary oil recovery techniques, referred to herein as improved oil recovery methods.

In an oil-bearing subterranean formation, oil, water, and sometimes gas, coexist in porous formation rock. Secondary recovery often involves injecting water into the formation via injection wells, in order to maintain pressure in the reservoir, and to drive the oil to producing wells. A disadvantage of using straight water to improve oil recovery is that water tends to move into the more highly permeable regions of rock, which are the easiest flow paths, and bypass the lower permeable rock. This results in uneven recovery of oil in the formation, where oil recovery is high in the highly permeable rock and the oil in the less permeable rock is left behind. Once the oil is recovered in the highly permeable zones, the zones become "watered-out" and increasing water is produced along with decreasing oil, making oil recovery uneconomic in a short time.

Secondary or tertiary oil recovery may involve adding a water-soluble polymer to the water injected into the formation in order to increase the viscosity of the water. This results in a more even flow of water into highly permeable and less permeable zones, and ultimately more oil recovery. The polymer performance can be improved substantially by crosslinking it after injection into the formation. Crosslinked polymer forms a gel in the formation rock in the highly permeable watered-out regions that selectively blocks these regions to additional flow of water. Because oil and water are immiscible, they occupy separate flow paths in the formation pores, so water flow in the rock is blocked to a much greater extent than oil flow with these water-soluble polymeric gels. The final result is higher oil recovery from the reservoir and less water production and recycling.

A material that is often used to crosslink polymeric materials in improved oil recovery operations is aluminum citrate. The trivalent aluminum metal acts as the active crosslinker for the polymer, and the citrate complexes the aluminum so that it is released slowly in the presence of the polymer after the solution is injected into the reservoir. A typical improved oil recovery operation may involve injection of a blended solution of dissolved water-soluble polymer and aluminum citrate into a reservoir over a period of several months.

A second area where gels are useful is in grouting operations. This would apply in certain construction projects where water encroachment is a problem. Grouts are injected into the subterranean formation to restrict the flow of water into the construction area. Grouts can also be used as a barrier to prohibit subterranean water movement in certain situations. For example, water encroachment on a foundation from a nearby pond might require use of a grout. Another use is in environmental remediation, where grouts can be used to temporarily block major water flow paths between a hazardous waste site and a potable water table.

When aluminum citrate was first used in the oilfield, according to U.S. Pat. No. 3,762,476 issued Oct. 2, 1973, aluminum sulfate hydrate and sodium citrate dihydrate were dry blended, then mixed with water at the desired concentration and pumped into the formation. There were several disadvantages of this method. First, the injected crosslinker solution had a very low pH, on the order of 2, which was corrosive to oilfield equipment. Second, the sulfate in the dry blend increased the tendency of certain oilfield waters to form sulfate scales. Third, the citrate and aluminum were not in contact for a sufficient time or in sufficient concentration for substantial chelation of the aluminum by the citrate to take place. As a result, aluminum release was more rapid, with premature and inconsistent gels formed too close to the wellbore, and aluminum lost to the formation via adsorption.

Manufacture of a liquid solution of aluminum citrate starting with aluminum chloride and aluminum sulfate is disclosed in British Patent No. 1,598,709. This liquid solution is unsuitable for improved oil recovery because the aluminum:citrate molar ratio is about 5.2:1, which results in unchelated aluminum in an acidic solution, with a pH of about 4 or less. The unchelated aluminum precipitates as the pH is increased to about 6.5, which is more suited for improved oil recovery. The maximum ratio of aluminum to citrate which allows for fully chelated aluminum is about 2.2:1.

An improvement over the original method of providing aluminum citrate to improved oil recovery projects was disclosed in U.S. Pat. No. 4,447,364. This method involves mixing a stable liquid aluminum citrate solution of pH 5.5 to 7.5 starting with aluminum chloride and citric acid. A 34 percent solution of aluminum chloride and a 50 percent solution of citric acid are blended such that the ratio of aluminum to citrate is from about 1.5:1 to 2:1. The pH of the acidic mixture is then adjusted upward with either ammonium hydroxide or sodium hydroxide. An intermediate aluminum citrate solution has an aluminum concentration of about 1 percent to 3 percent by weight. The final solution has an aluminum concentration of about 2.25 to about 3% by weight. The aluminum is fully chelated by the citrate. This is the current preferred solution for oilfield use. In certain situations, the practical use of this aluminum citrate solution is limited. Transportation of the liquid product to remote areas is expensive due to the relatively low active aluminum concentration. Ground transport is extremely expensive over long distances because the liquid product must be hauled in a tanker, which is usually full one way and empty on the return trip. Because the final product is a liquid, it must be either stored indoors or in a heated tank in extremely cold areas, where the temperature drops below about −20° F. Therefore, desirable improvements over the current technology include increasing the active aluminum concentration in the solution and making a dry aluminum citrate product which can be more easily transported over long distances and stored under harsh environmental circumstances.

An alternative method of mixing liquid aluminum citrate, starting with sodium aluminate, is disclosed in U.S. Pat. No. 4,601,340. The citrate source is either sodium citrate or citric acid. The concentration of the final product may be from 3 to 3.5 percent by weight of aluminum, but the patent teaches that the aluminum concentration should be no greater than about 3 percent by weight.

Aluminum citrate compositions having a molar ratio of 1:1 aluminum to citrate have been disclosed, but this ratio is too low for practical use in gels because the aluminum is too tightly bound by the citrate, and therefore takes a long time to react with the polymer. U.S. Pat. Nos. 3,200,136 and 2,327,815 discuss the preparation of very dilute solutions with a 1:1 molar ratio of aluminum:citrate. The aluminum concentrations, which are much less than that provided by the current technology, are too low for practical use in subterranean formations. In U.S. Pat. No. 3,200,136, example 5 discloses a solid aluminum citrate material with an aluminum:citrate ratio of 2:1 which has a solution pH of about 3 at 10 percent solution, which would give a substantially lower pH in solutions having aluminum concentrations of 3 percent or more by weight. A pH of 3 is too low for practical use in gels. U.S. Pat. No. 2,327,815 discloses an aluminum citrate salt which is a 100 percent basic complex and does not have a chloride component. A solid aluminum citrate material made from aluminum nitrate and citric acid is discussed by Feng, et al., "Aluminum Citrate: Isolate and Structural Characterization of a Stable Trinuclear Complex," Inorg. Chem. (1990) 29:408–411, but again, the active aluminum concentration is too low for practical use.

Other liquid preparations comprising aluminum citrate in solution are known. See, e.g., Gallet, J. P. and Paris, R. A., "Etude Thermometrique de la Formation des Complexes du Fer(III), de L'Aluminium et du Gallium," Anal. Chim. Acta (1967) 39:341–348; Weise, G. and Veith, J. A., "Komplexbidung Zwischen Zitronensaure und Aluminium," Z. Naturforsch. (1975) 30b:446–453; Karlik, S. J. et al., "Aluminum-27 Nuclear Magnetic Resonance Study of Aluminum(III) Interactions with Carboxylate Ligands," Inorg. Chem. (1983) 22:525–529; Ohman, L. O. and Sjoberg, S., "Equilibrium and Structural Studies of Silicon(IV) and Aluminum(III) in Aqueous Solution. Part 9. A Potentiometric Study of Mono- and Poly-nuclear Aluminum(III) Citrates," J. Chem. Soc. Dalton Trans. (1983) pp. 2513–2517; Mak, M. K. S. and Langford, C. H., "Kinetic Analysis Applied to Aluminum Citrate Complexing," Inorg. Chim. Acta (1983) 70:237–246; Lopez-Quintela, M. A. et al., "Kinetics and Thermodynamics of Complex Formation Between Aluminum(III) and Citric Acid in Aqueous Solution," J. Chem. Soc. Faraday Trans. I (1984) 80:2313–2321; Gregor, J. E. and Powell, H. K. J., "Aluminum(III)-Citrate Complexes: a Potentiometric and $^{13}$C N.M.R. Study," Aust. J. Chem. (1986) 39:1851–1864; Ohman, L. O., "Equilibrium and Structural Studies of Silicon(IV) and Aluminum(III) in Aqueous Solution. 17. Stable and Metastable Complexes in the System $H^+$-$Al^{3+}$-Citric Acid," Inorg. Chem. (1988) 27:2565–2570; Shioyama, T. K. and Little, R. A., U.S. Pat. No. 4,560,783; and No. 4,601,340. However, to Applicant's knowledge, no previous workers have been able to achieve stable aluminum citrate solutions having greater than 3.0 weight percent aluminum.

Aluminum citrate solutions have been used in oil recovery processes as described, e.g., in Mack, J., "Process Technology Improves Oil Recovery," Oil & Gas J. (1979) pp.67–71; Parmeswar, R. and Willhite, S., "A Study of the Reduction of Brine Permeability in Berea Sandstone With the Aluminum Citrate Process," SPE Reservoir Eng. (1988) pp. 959–966; and U.S. Pat. Nos. 3,762,476, 3,833,061, 3,952,806, 3,981,363, 4,018,286, 4,039,029, 4,120,361, 4,413,680, 4,488,601, 4,498,539, 4,526,231, 4,569,393, 4,579,176, 4,657,944, 4,644,193 and 5,151,615.

Aluminum citrate solutions have also been used in polymerization processes (as described in U.S. Pat. Nos. 3,533,973 and 3,839,255) and in pharmaceutical and related products (as described in U.S. Pat. Nos. 3,874,390, 3,924,642, 4,274,427, 4,645,662, 4,591,384, and 5,162,378). Miscellaneous industrial uses of aluminum citrate solutions include those described in U.S. Pat. Nos. 3,898,186, 3,910,805, 3,964,255, 4,116,931 and 4,612,175. Again, applicant is aware of no such solutions containing greater than 3.0 weight percent aluminum.

Recently a dry aluminum citrate material was developed by Haarman & Reimer, Elkhart, Ind., with two samples privately submitted to the inventor for evaluation. The first sample contained 10.99 percent aluminum and 1 percent chloride, with about 8 percent of the material unaccounted for. The second sample contained 10.21 percent aluminum and 0.3 percent chloride, with about 14 percent of the material unaccounted for. The test results on these two dry aluminum citrate samples suggest that both materials were made with a source of aluminum which is relatively free of chloride. A source of aluminum which is in a chloride form is desirable for making an aluminum citrate product, because the chloride, which will be present in the final product, is generally a non-scaling ion when mixed with water prior to subterranean injection.

U.S. Pat. Nos. 3,294,860, 4,888,136, 4,898,842, 3,674,726 and 5,019,401, and Japanese Patent No. 92065802 mention the existence of an aluminum citrate product as a powder or salt; however, no methods for making such a product are taught. No commercial source of a dry aluminum citrate product has been found by applicant herein. References to commercial availability of such a product in the prior art appear to be erroneous.

All publications and patents referred to herein are incorporated by reference in their entirety.

SUMMARY OF THE INVENTION

An aluminum citrate preparation is provided in dry form having at least about 7 percent aluminum by weight, at least about 1.1 percent chloride by weight, and a molar ratio of aluminum to citrate of between about 0.5:1 and about 2.2:1. The preparation is suitable for use in secondary and tertiary oil recovery and is substantially free of sulfate so as to avoid undesirable scaling. These preparations are also substantially free of nitrate.

The term "aluminum citrate preparation" refers to a product predominantly comprising aluminum and citrate.

Depending on the method of making the dry aluminum citrate preparation of this invention, it may have an aluminum:chloride molar ratio of at least about 1:3 and up to about 2:1, preferably about 2:1. In a preferred embodiment, the aluminum citrate preparation of this invention has at least about 11 percent aluminum by weight.

A method for making a dry aluminum citrate preparation of this invention comprises:

a. providing a first aqueous solution comprising an aluminum-chloride-containing complex wherein the aluminum:chloride molar ratio is at least about 1:3;

b. mixing said first solution with a second solution comprising citric acid to form a composition wherein the molar ratio of aluminum:citrate is at most about 2.2:1;

c. stirring said composition of step b. continuously at a rate sufficient to keep the resultant slurry in motion;

d. adjusting the pH of said composition to between about 5.0 and about 9.0;

e. drying said composition.

The drying step may be carried out by any means known to the art and is preferably carried out using drum drying means.

This dry aluminum citrate preparation, when solubilized in water or an aqueous medium, will form an aqueous solution having a pH between about 5.0 and about 9.0 at a concentration of up to about 3 percent by weight aluminum. Liquid aluminum citrate preparations of this invention may be made by solubilizing dry aluminum citrate preparations of this invention in aqueous media.

Liquid aluminum citrate preparations of this invention, more accurately referred to as solutions comprising aluminum citrate complex, may also be prepared by the following method:

a. providing a first aqueous solution comprising an aluminum-chloride-containing complex wherein the aluminum:chloride ratio is at least about 1:3;

b. mixing said first solution with a second solution comprising citric acid to form a composition having a molar ratio of aluminum:citrate at most about 2.2:1;

c. stirring said composition of step b. continuously at a rate sufficient to keep the resultant slurry in motion;

d. adjusting the pH of said composition to between about 5.0 and about 9.0.

The pH adjustment of step d. is preferably carried out with a concentrated basic hydroxide solution of the formula MOH, where M is an alkali metal or ammonium cation. The aluminum-chloride-containing complex is preferably provided in the form of aluminum chlorohydrate solution having a molar ratio of aluminum:chloride of about 1:2, a concentration of up to about 50 percent by weight and an aluminum concentration of up to about 12.5 percent by weight. The aluminum-chloride-containing complex may also be provided in the form of a mixture of aluminum chlorohydrate and polyaluminum chloride solution, said polyaluminum chloride solution having an activity of between about 25 percent and about 34 percent by weight, and a molar ratio of aluminum:chloride of at least about 1:3 aluminum:chloride.

Liquid aluminum citrate preparations of this invention have at least about 3.1 percent by weight aluminum, a pH between about 5.0 and about 9.0, a molar ratio of aluminum to citrate at least about 0.5:1 and at most about 2.2:1, and are essentially free of sulfate and nitrate. The molar ratio of aluminum to chloride is between about 1:3 and about 2:1, preferably about 2:1. Preferably such preparations have at least about 1.1 percent chloride by weight.

The dry aluminum citrate composition of this invention may be used in combination with a water-soluble polymer to form a permeability-modifying composition in dry form comprising a mixture of such polymer capable of cross linking in the presence of water and aluminum ions, and aluminum citrate having at least about 7 percent aluminum by weight, at least about 1.1 percent chloride by weight, and a molar ratio of aluminum to citrate of between about 0.5:1 and about 2.2:1 in an amount sufficient to enhance cross linking of said polymer.

Any polymer known to the art may be used; preferably the polymer is selected from the group consisting of polyacrylamide, partially hydrolyzed polyacrylamide, carboxymethylcellulose, polyvinyl alcohol, polystyrene sulfonates, polyvinylpyrrolidone, AMPS (2-acrylamide-2-methyl propane sulfonate), and combinations thereof. Preferably the polymer is partially hydrolyzed polyacrylamide.

A process for decreasing the water permeability of a subterranean formation using a liquid aluminum citrate preparation of this invention comprises:

a. injecting into the formation an aqueous solution comprising a water-soluble polymer capable of cross linking in the presence of water and aluminum ions;

b. be subsequently injecting into the formation an aqueous solution comprising aluminum citrate having at least about 3.1 percent by weight aluminum, a pH between about 5.0 and about 9.0 and a molar ratio of aluminum to citrate at most about 2.2:1 in an amount sufficient to enhance cross linking of said polymer.

The aqueous solution comprising a polymer of step a. preferably comprises about 50 to about 20,000 ppm of a polymer selected from the group consisting of polyacrylamide, partially hydrolyzed polyacrylamide, carboxymethylcellulose, polyvinyl alcohol, polystyrene sulfonates, polyvinylpyrrolidone, AMPS (2-acrylamide-2-methyl propane sulfonate), and combinations thereof.

Alternatively, the aqueous solutions of polymer and aluminum citrate may be mixed prior to injection into the formation. In this case, the method comprises injecting into the formation an aqueous solution comprising a water-soluble polymer capable of cross linking in the presence of water and aluminum ions, an aluminum citrate solution having at least about 3.1 percent aluminum by weight of solutions at a pH between about 5.0 and about 9.0 and a molar ratio of aluminum to citrate at most about 2.2:1, said aluminum being present in an amount sufficient to enhance cross linking of said polymer.

The aluminum citrate may be provided to the injection site in the form of a dry aluminum citrate preparation of this invention and solubilized just prior to injection, or may be provided in the form of a liquid aluminum citrate preparation of this invention.

When a dry aluminum citrate composition is used, one method of this invention for decreasing the water permeability of a subterranean formation comprises:

a. mixing (a) a dry composition comprising a water-soluble polymer capable of cross linking in the presence of water and aluminum ions, and (b) a dry aluminum citrate preparation having at least about 7 percent aluminum by weight, at least about 1.1 percent chloride by weight, and a molar ratio of aluminum to citrate of between about 0.5:1 and about 2.2:1 in an amount sufficient to enhance cross linking of said polymer, with (c) an aqueous solution;

b. injecting said aqueous solution into the formation.

DETAILED DESCRIPTION OF THE PREFERRED EMBODIMENTS

A preferred embodiment of this invention involves first making a concentrated aluminum citrate solution, then drying the solution to increase the activity and transportability if desired and finally using the product to form gels in a subterranean formation.

The liquid aluminum citrate solution is mixed according to the following process:

a. Provide an aqueous solution of an aluminum-chloride complex having a molar ratio of aluminum to chloride greater than 1:3. A suitable material is a solution of aluminum chlorohydrate, which has a molar ratio of aluminum to chloride of about 2:1 and an active aluminum concentration of about 12.5 percent.

b. Add a sufficient quantity of an aqueous solution comprising citric acid such that the desired aluminum:citrate ratio is attained. A solution of 50 percent citric acid is suitable. The molar ratio of aluminum to citrate should be less than about 2.2:1.

c. Allow the resultant acidic slurry mixture of the above two components to agitate at a rate sufficient to keep the fine particles of the slurry moving.

d. Adjust the pH of the acidic mixture to between about 5.0 and 9.0 while stirring, preferably to about 6.9, by adding a strong basic solution while agitating vigorously. Aqua ammonia, which provides ammonium hydroxide at about 30 percent by weight, works well.

e. The final aluminum citrate solution will have an active aluminum concentration greater than about 3.1 percent by weight and preferably greater than about 3.5 to about 4.5 percent by weight.

If a more concentrated dry aluminum citrate material is needed in order to simplify long-distance shipping or storage under difficult environmental circumstances, the liquid product may be dried by a number of conventional methods, such as spray drying, drum drying, crystallization or any suitable evaporative technique. It is possible to increase the aluminum concentration in the dry product to at least about 11 percent to 16.5 percent by weight.

The aluminum citrate product can be used in either liquid or dry form to crosslink polymer in an aqueous solution for use as a water-blocking gel in a subterranean formation. In the liquid form, the aluminum citrate solution is mixed with an aqueous solution of polymer, then the mixture is injected into the formation. In the dry form, the aluminum citrate may generally be used in several ways. In one way, the aluminum citrate is dissolved in water, then mixed with an aqueous solution of the polymer, then the mixture is injected into the formation. In another, the dry aluminum citrate is mixed with a dry water-soluble polymeric material to form a combination dry product, which is then dissolved and injected into the formation. A third way to use the dry aluminum citrate product is to add it directly to the aqueous polymer solution, then inject the mixture into the formation.

This invention provides a new aluminum citrate product which is an improvement over current technology in the following specific areas:

1. The liquid product can be mixed at up to about 5.1 weight percent aluminum, which is much higher than the current technology limit of 3 percent.

2. The product is substantially free of sulfate and nitrate and contains less chloride than prior products made using aluminum chloride starting materials, which increases the aluminum concentration.

3. The amount of basic hydroxide required for neutralization of a given amount of aluminum citrate is up to two thirds less than that required in conventional technology.

4. The liquid product can be dried to obtain a concentration of at least 7 percent by weight aluminum, and up to about 16.5 percent by weight, with a preferred concentration of about 13 percent by weight aluminum.

5. The dry product is simpler than liquid product to transport and store, especially under difficult circumstances such as remote field locations and extremely cold environments.

6. The blended dry aluminum citrate/polymer product is simpler to feed because no extra chemical pump is required to add the aluminum citrate to the aqueous polymer, as there is with a liquid aluminum citrate product.

The liquid aluminum citrate product is made by first blending an aqueous solution of aluminum chlorohydrate with an aqueous solution of citric acid while maintaining sufficient agitation to keep the entire mixture moving throughout the reaction vessel. The aluminum chloride solution can be any concentration up to about 50 percent by weight, preferably in the range of about 20 to about 50 percent and most preferably about 37.5 percent. The citric acid solution can be any concentration up to about 60 percent, with about 50 percent being the preferred concentration. The mixture of aluminum chlorohydrate and citric acid is acidic with a pH of about 1.0 to about 2.0 if the preferred concentrations are used. Immediately after blending the two materials, some heat is released, causing the mixture to warm slightly. When the aluminum chlorohydrate solution and the citric acid are mixed together, the mixture is initially clear, but within about 20 to 30 minutes it begins to develop a precipitate and becomes a slurry full of fine white particles within about an hour.

The slurry must be kept moving at a rate sufficient to keep the particles from settling. Also, the reaction vessel must be free of stagnant regions where particles could build over time. If the slurry is allowed to stop moving and the particles do settle due to a power outage or breakdown of the agitator, the agitation should be resumed again as soon as possible. If the agitation is resumed within about 24 hours, the slurry can still be used to provide a clear final product. If the slurry remains still for much more than about 24 hours, the final product will be cloudy, with cloudiness increasing proportional to the time the slurry is allowed to sit.

After the slurry has been allowed to agitate, the pH is adjusted upward. The pH can be adjusted upward any time after the aluminum chlorohydrate and citric acid are blended, but a higher quality final product will be obtained if the slurry is allowed to stir for about ½ hour to about 24 hours, more preferably about 1 to about 6 hours and most preferably about 2 hours. Any strong base in aqueous solution can be used to adjust the pH upward, including but not limited to ammonium hydroxide, sodium hydroxide or potassium hydroxide. Ammonium hydroxide is preferred because it is a strong base and the ammonium cation has the lowest molecular weight, with the final result being a final product which is more concentrated in aluminum. Concentrated ammonium hydroxide in water (aqua ammonia) has a concentration of about 30 percent by weight. The aqua ammonia is added to the acidic slurry while agitating until the pH of the solution reaches about 5.0 to about 9.0, preferably about 6.0 to about 8.0 and most preferably about 6.7 to 6.9. During the pH increase, the slurry thickens considerably over a short pH range from about 3 to 4; because of this, it is important to keep the solution moving with vigorous agitation during the pH increase. Depending on how long the slurry was allowed to stir before pH adjustment, it will thin and clear when the pH is increased above about 5 to 6. The final product is crystal clear with no evidence of precipitate. As the solution nears the pH endpoint, the base addition should be slowed, and the final pH adjustment should be carried out over a period of about 1 to about 2 hours. The pH may creep either up or down, depending on the desired endpoint, over the following 24 hours, so a final pH adjustment about 24 hours after mixing is also advisable.

The final liquid aluminum citrate product made by this invention is a clear, blond colored solution with an aluminum content of at least about 3.1 to about 5.1 percent by weight, with a molar ratio of aluminum to citrate of less than about 2.2:1, depending on the initial concentrations of the aluminum chlorohydrate and citric acid solutions. The product is stable for several months on standing. Stability of the product is best if the pH is adjusted to at least about 6.5; if a lower pH is used the product should be used or diluted soon after mixing. The amount of time the acid slurry is allowed to agitate before pH adjustment also has an effect on shelf life. If the pH is adjusted immediately after the aluminum chlorohydrate and citric acid solutions are mixed, the final solution will be clear initially, but will begin to develop cloudiness and thicken within about a week. The solution will become progressively thicker and cloudier over the next few weeks, until it becomes a thick white paste. The thick white paste is soluble in water to form a clear solution at concentrations of about 1 percent or less, but it is difficult to handle on a large scale unless special equipment is employed. The only case in which immediate adjustment of the pH is advisable is when the intention is to dry the product immediately; in this case the dry product has good solubility in water at the low concentrations at which it will be used. If the intention is to mix a liquid product which may stand for several months before using, the slurry should be allowed to stir for at least about 15 minutes, more preferably about 30 minutes to about an hour and most preferably about 2 to 3 hours. The slurry can be left to stir for up to three weeks before pH adjustment with a clear final solution obtained after pH adjustment. If the slurry is stirred for more than about 3 weeks the final product is slightly cloudy rather than clear.

The maximum aluminum concentration in the final liquid product is about 5.1 weight percent, and this can only be obtained if the initial acid slurry is mixed using about 50 percent aluminum chlorohydrate and about 50 percent citric acid, with a molar ratio of about 1.9:1 aluminum to citrate. This solution is clear and stable for several months on standing, but is difficult to make on a large scale because the slurry is extremely thick at its peak and it is difficult to maintain agitation sufficient to prevent the particles from "hanging up" on the sides of the reaction vessel. When the particles do hang up they tend to build up and it is difficult to get them moving again. The final result when this happens is a cloudy final product. The main use for this highly concentrated material is to make product intended for drying, to minimize the energy needed to dry the product.

The minimum aluminum concentration in the final liquid product should be about 3.1 percent, which can be obtained by diluting the aluminum chlorohydrate to a concentration of about 20 percent by weight before mixing with about 50 percent citric acid. Dilution of the aluminum chlorohydrate results in less severe thickening of the slurry during the pH adjustment, so agitation requirements are not as rigorous. However, at this low aluminum concentration the energy required for drying is increased, so this is not recommended for products intended for drying.

The preferred maximum aluminum concentration in the final aluminum citrate product is about 4.6 percent by weight. This is obtained by diluting the aluminum chlorohydrate to about 37.5 percent with water before mixing with the 50 percent citric acid. In this case, the slurry stage during pH adjustment does not thicken to a degree such that agitation is extremely difficult. This is therefore an optimum final aluminum concentration to work with. The solution is stable for several months on standing as a liquid, and can be dried with less energy required relative to the 3.1 percent aluminum solution.

When aluminum chlorohydrate is used to make the aluminum citrate product, the chloride concentration is minimized, because the molar ratio of aluminum to chloride in aluminum chlorohydrate is about 2:1. With current technology, this is the highest ratio of aluminum to chloride available in an aqueous solution. While the chloride is considered benign in the final product in terms of interfering with product efficacy or causing scale formation, it is desirable to minimize the chloride concentration so that the aluminum citrate concentration in the final product is maximized. However, there may also be cases where other sources of aluminum, such as polyaluminum chloride, or aluminum chloride are more readily available or sufficiently less costly than aluminum chlorohydrate to justify their use. The current technology involves the use of straight aluminum chloride, which has a molar ratio of aluminum to chloride of 1:3, so that much more chloride is present in the final product. This can be improved by mixing aluminum chloride with aluminum chlorohydrate in any ratio in order to increase the molar ratio of aluminum to chloride and minimize the chloride concentration in the final product. In this case, the aluminum to chloride molar ratio in the final product will be in the range of about 1:3 to about 2:1, where the aluminum chlorohydrate is used to upgrade the aluminum chloride for the purpose of increasing the aluminum concentration in the final product. After the two aluminum sources are mixed together, the citric acid solution can be added to form the acidic slurry, then the pH can be increased as described above.

If the aluminum citrate product is intended for shipment over extremely long distances or for use and storage in extremely harsh environments where temperatures frequently drop below freezing the product can be dried to simplify operations. The material dries easily and can be dried using any common industrial drying technique. The Applicant has worked with evaporation, crystallization and spray drying, and has found evaporation via drum drying to work best.

Aluminum citrate can be evaporated at temperatures ranging from about 35° C. to about 200° C, preferably in the range about 45° C. to about 105° C. and most preferably at about 85° C. In the optimum temperature range of 45° C. to 105° C., the dried product is a white solid made up of a combination of translucent crystals, white crystals, and white amorphous powder. The product has a dry density similar to sodium chloride salt. The product has a solubility of about 15 percent and redissolves readily to form a crystal-clear solution with a pH that is close to the original pH of the liquid product prior to drying. The aluminum concentration in the dry product depends on the aluminum source in the liquid product and the molar ratio of aluminum:citrate. For example, if the aluminum source is aluminum chlorohydrate and the aluminum:citrate ratio is 1.9:1, the aluminum concentration in the final dried product is about 12.0–13.5 percent aluminum if dried in the optimum temperature range. If the aluminum source is a blend of aluminum chlorohydrate and polyaluminum chloride, the aluminum content in the final dry product decreases as the polyaluminum chloride in the blend is increased. If 100 percent polyaluminum chloride is used to make the liquid product, the aluminum concentration in the final dry product is about 7 to 8 percent.

When the material is dried in the optimum temperature range, the final product contains about 3–5 percent moisture. By drying at higher temperatures of about 150° C. to about 200° C. the product can be dried further in order to decrease the moisture and increase the aluminum content, to a maximum of about 16.5 percent. However, when the product is dried at this high temperature it may "burn," resulting in a darkened product with limited solubility. Also, the product is more hygroscopic when the moisture content is driven below about 3–5 percent. At the lowest drying temperature of about 35° C., the product dries, but the time required for complete drying is excessive and the final product is only about 12.0 percent aluminum. The drying time decreases and the aluminum concentration increases as the drying temperature is increased to about 75° C. to 85° C. At 85° C., the aluminum concentration in the dried product is about 13.5 percent. Beyond about 85° C. the aluminum concentration does not increase further, so this temperature represents the optimum temperature for drying.

On a large scale, an excellent means of drying the product is to use a drum dryer. The aluminum citrate dries readily on a drum dryer. In a field test using a double drum dryer at a temperature of 65° C., dry aluminum citrate product was produced at a rate of 250 pounds/hour.

Spray drying also has been pilot tested and has potential on a large scale, with optimization of the process to improve the consistency of the dried product. When aluminum citrate is spray dried, the final product tends to have a light, fluffy consistency which is difficult to transport on a large scale because of the high volume taken up by the dried material. One way to remedy this problem would be to pelletize the spray dried material, but this would add to the cost of the final product.

The aluminum citrate product in either dry or liquid form can be used to crosslink water-soluble polymeric materials to form gels in subterranean formations. Gels are commonly used in oilfield enhanced oil recovery processes to selectively block areas of rock to further penetration by water. A common practice is to first dissolve the polymeric material in water using a chemical feed system designed to dissolve the polymer, then add the crosslinker using a positive displacement type chemical pump to the dissolved polymer downstream, so that the polymer and crosslinker are mixed in the water before the solution begins to move down the wellbore and into the subterranean formation. Another common practice that has been described in U.S. Pat. Nos. 3,762,476, 3,833,061, 3,952,806, 4,120,361, 4,488,601 and 4,498,539, is to inject the concentrated aluminum citrate solution and the aqueous polymer solutions separately, so the polymer and aluminum are essentially separated until they have entered the subterranean formation and have had time to mix in situ. As with the first practice, the polymer is added to the water using a suitable polymer feed system, and the aluminum is added via a chemical pump. The liquid aluminum citrate product described in this invention can be used as a crosslinker according to either of these common practices. The dry aluminum citrate product is more versatile and can be used in a number of ways, including but not limited to the following three possibilities:

1) Mix the dry aluminum citrate with water to obtain a concentrated solution, then inject the solution downstream of the polymer injection, according to common practice. This practice is known as continuous gel injection.

2) Mix the dry aluminum citrate with water to form a concentrated solution, then inject this solution separately, followed by separate polymer solution injection according to common practice. This practice is known as layered gel injection.

3) Blend the dry aluminum citrate with a suitable dry polymeric material. The blended dry product can then be added to the injection water using a suitable dry chemical feed system.

In the first two embodiments, the dry aluminum citrate is simply mixed with water to obtain a concentrated aqueous solution, then the aqueous solution is used according to common practice. The third embodiment is unique and can only be practiced where both the aluminum citrate product and the polymeric material are dry products and are water soluble. The dry blend provides a very convenient means of using crosslinked polymer, because the single blended product can be injected using only a suitable dry chemical feed system without the need for an addition chemical pump and liquid storage facilities downstream of the polymer feed system. Thus, a project operator saves upfront capital costs when preparing a site for gel injection.

There are many water-soluble polymeric materials that can be used for subterranean gels, including, but not limited to polyacrylamide, partially hydrolyzed polyacrylamide, carboxymethylcellulose, polyvinyl alcohol, polystyrene sulfonates, polyvinylpyrrolidone, AMPS (2-acrylamide-2-methyl propane sulfonate), or any combination of these materials. The most common embodiments use partially hydrolyzed polyacrylamide (HPAM) and HPAM/AMPS copolymers. The polymer should have a high molecular weight, of about 1 to about 30 million, more preferably about 10 to about 30 million and most preferably about 20 to about 30 million. When a higher molecular weight polymer is used, a lower polymer concentration is required to obtain a given gel strength. The polymer must have some negative charge in the form of hydrolysis groups; the charge should be in the range of about 0.1 to about 50 percent, more preferably about 5 to about 40 percent and most preferably about 10 to about 30 percent. The negative charge on the polymer influences the rate of cross linking and, to an extent, the strength of the final gel. A higher negative charge leads to faster crosslinking and a stronger final gel.

Polymer concentrations can range from about 50 to about 20,000 ppm, preferably from 100 to 3000 ppm and most preferably from about 150 to about 1200 ppm. At the extreme low end of the polymer concentration range, gel formation is very slow, allowing the gellable polymer mixture to be injected well into the subterranean formation before gel formation; however, the gels are extremely weak and only work well in formations with relatively low permeability, on the order of 10–50 md. At the extreme high end of the concentration range, strong gels tend to form relatively quickly, so the gels should only be used in cases where deep penetration is not needed or desired. This may apply in cases where it is desired to block fracture systems close to either an injection or a producing wellbore. In the optimum concentration range of about 150 to about 1200 ppm polymer, colloidal dispersion gels are formed which can be placed deep in a subterranean formation where they can be used to block large areas of highly permeable rock to the flow of water. The polymer concentrations in this range allow gel formation rates which are sufficiently slow to place the gel deep in the formation, yet the gels are strong enough to block highly permeable areas of rock to the flow of water. Over the optimum concentration range, lower polymer concentrations, on the order of about 150 to about 600 ppm, work well in situations where a relatively fresh water (<3 percent by weight total dissolved solids) is available for injection and the average permeability of the affected subterranean formation is less than about 1000 md. Higher polymer concentrations are needed in situations where the injection supply water has a relatively high total dissolved solids content (>3 percent by weight total dissolved solids) or where the permeability of the affected subterranean formation is greater than about 1000 md.

The aluminum concentration in the gel depends on the polymer concentration, water makeup and gel strength and formation time desired. Because aluminum concentrations depend on polymer concentrations, aluminum concentrations are often expressed as polymer:aluminum ratios. In the gel process described herein, the polymer:aluminum ratio can range from about 1:1 to about 1000:1. The lower ratios in the range of about 1:1 to about 1:10 are best used in relatively high salinity brines, with total dissolved solids concentrations greater than about 3 percent by weight; in this type of brine the additional aluminum citrate can better compete with the ions present in the brine for gel reaction sites on the polymer molecules. Higher polymer:aluminum ratios of about 1:10 to about 1:1000, more preferably about 1:10 to about 1:200, and most preferably about 1:10 to about 1:100 can, be used when the injection supply water is relatively fresh, with less than about 3 percent total dissolved solids.

Gels comprised of a polymeric material and the aluminum citrate product described herein either in liquid or dry form can be used in a variety of processes where blockage of highly permeable regions of subterranean formations are needed. In enhanced oil recovery, the gels can be injected following injection of an aqueous solution of cationic polyacrylamide. In this process, the cationic polyacrylamide provides a layer of cationic sites on the rock surfaces, which are generally anionic, and the subsequent gel adheres to the cationic sites creating a very strong blockage in the affected rock. The gel can also be injected following injection of a strong potassium hydroxide (KOH) solution, which is used to stabilize clays in subterranean formations as described in U.S. Pat. No. 4,280,560. In this case, the entire process involves injection of a potassium chloride (KCl) spacer, followed by KOH, followed by another spacer to move unreacted KOH out of the area, followed by the polymeric/aluminum citrate gel. The gel blocks the most permeable rock to further flow of water, allowing subsequent water injection to sweep residual oil out of the less permeable rock. Enhanced oil recovery processes commonly involve injection of aqueous surface-active solutions designed to "wash" oil out of subterranean rock by lowering the interfacial tension between the oil and the injection water. Surface-active solutions may comprise alkaline agents, surfactants, combinations of surfactants and alkaline agents, and combinations of surfactants, alkaline agents and polymeric materials. Polymeric/aluminum citrate gels can be injected before, between and after injection of surface-active slugs to prevent further entry of injection solutions into highly permeable rock which has been washed out by the surface-active solutions. Another commonly employed enhanced oil recovery process is imbibition, in which chemicals are injected to promote water entry into tight rock, so the water can better drive the oil out of these hard-to-reach places in the subterranean formation. In this case, the gels may be used to block the more permeable, washed out rock prior to the imbibition process. Polymeric/aluminum citrate gels can also be used in conjunction with other gel process. In this case a gel intended for use near an injection wellbore such as that described in U.S. Pat. No. 4,683,949 might be used to divert the flow of subsequent polymer/aluminum citrate gel, which could then penetrate deeper into the formation.

In civil service, injection of polymeric aluminum citrate gels can be used in place of conventional grouting operations. Typically, grouting is used to prevent water encroachment into a civil service project, such as constructing a tunnel below the water table. A problem with many types of grouts, such as cements and resins, is that penetration into the subterranean strata is limited, and the relatively thin expanse of grout is subject to high stress, creating the need for frequent repairs. A polymeric/aluminum citrate gel can be injected much deeper into the strata and can affect a relatively large volume of strata. The result is a longer-lasting blocking effect and little or no requirement for repairs.

In the environmental remediation and cleanup field, there is a need for in-depth blockage of subterranean strata. A typical case might involve an abandoned mine site, where metals have leached into groundwater. In this case the gel can be injected into the permeable region of subterranean strata where it provides a barrier between the mine site and the groundwater formation.

The methods of practicing the invention are illustrated by the following examples:

EXAMPLE 1

The following batch was mixed in the laboratory and illustrates a high concentration of aluminum for a final liquid product with a molar ratio of aluminum to citrate of 1.9:1. To a 300 ml beaker, 60 grams of 50 percent aluminum chlorohydrate solution was added, followed by 20 grams of deionized water. 56.14 grams of 50 percent citric acid was added to the dilute aluminum chlorohydrate all at once, then the solution was stirred using a magnetic stirrer at a medium rate. The solution was allowed to stir for 30 minutes. After about 15 minutes of stirring, the solution began to develop turbidity, and after 30 minutes the solution was extremely cloudy with a very fine, white precipitate. At this point, aqua ammonia addition was commenced. The initial pH at the start of the aqua addition was about 1.30. As the aqua was added, the pH increased and the slurry increased in cloudiness and thickness, peaking at a pH of about 3 to 4. As more aqua was added, the pH continued to increase and the solution began to thin and decrease in turbidity, up to a pH of 6.45, where it cleared completely. The pH was increased further to 6.90 over the next hour, then the finished solution was stored. The total aqua used was 30.86 ml. The aluminum concentration in the final aluminum citrate product was 4.60 percent by weight.

EXAMPLE 2

The purpose of this example is to illustrate the effect of temperature on drying of the aluminum citrate product. A liquid aluminum citrate solution was mixed, starting with 201.71 grams 50 percent aluminum chlorohydrate, 303.09 grams deionized water and 188.63 grams 50 percent citric acid, in a 1000 ml beaker. The solution was allowed to stir for 30 minutes using an overhead stirrer. A total of 104.6 ml aqua ammonia was added as described in Example 1, to increase the pH of the mixture to 6.9. The solution was then divided into 9 parts and dried at 9 different temperatures. The results are summarized in the following table.

| Drying Temperature °C. | Moisture Removed % | Active Aluminum in Dry Product, % |
| --- | --- | --- |
| 45 | 74.0 | 12.4 |
| 55 | 74.8 | 12.7 |
| 65 | 75.1 | 12.8 |
| 72 | 75.3 | 13.0 |
| 85 | 76.2 | 13.5 |
| 95 | 75.6 | 13.1 |
| 105 | 75.8 | 13.2 |
| 145 | 78.5 | 13.7 |
| 185 | 81.3 | 15.8 |

The product that was dried at temperatures from 45° C. to 105° C. was white in color with a yellow tint. The dry particles were mostly granular, with some amorphous dusty solid also present. It dissolved readily in water to form a clear solution at 15 percent by weight. The two samples that were dried at the higher temperatures of 145° and 185° C. were dark brown and black, respectively. Both of these materials were limited in solubility, with only about a 500 ppm solution possible.

EXAMPLE 3

The purpose of this example is to illustrate drying of an aluminum citrate product made using previous technology, starting with aluminum chloride. The active aluminum concentration in this dried product represents the lower limit of the technology introduced in this patent. 358.3 grams of 26.11 percent aluminum chloride was added to a 1000 ml beaker, followed by 148.8 grams of 50 percent citric acid. The acidic solution was allowed to stir for 1 hour, after which time it was still clear, with no evidence of precipitate. After this time, aqua ammonia was added to increase the pH. The solution went through a slurry stage as the aqua was added, then cleared at a pH of about 6.5. The pH was raised to 6.8, then the solution was drum-dried at 80° C. The dried material was a white, flaky material which crumbled easily and contained a lot of fine white dust. The aluminum concentration was 7.5 percent by weight, and the amount of moisture removed was 66.6 percent. Compared to the product made by drying aluminum chlorohydrate in Example 2 at 85° C. the aluminum concentration in the dry material starting with aluminum chloride was about 5 percent less by weight.

EXAMPLE 4

This example illustrates the use of liquid aluminum citrate made from aluminum chlorohydrate in colloidal dispersion gels. In the lab, a solution of 300 ppm partially hydrolyzed polyacrylamide was mixed in an aqueous solution of 0.5 percent KCl. The polymer was a copolymer of acrylamide and sodium salt of carboxylic acid, with a viscosity average molecular weight of about 25 million and a carboxylate content of about 25 percent. To each polymer solution was added liquid aluminum citrate made from aluminum chlorohydrate. The purpose of adding the aluminum citrate to the polymer solutions was to form gels suitable for blocking the flow of water in subterranean formations. To determine whether the gels were capable of blocking a porous media, the gels were tested by flowing under differential pressure through screen packs made of five 100-mesh stainless steel screens stacked tightly on top of each other. The screen pack provides a simulated porous media. The flow test data is used to determine "transition pressures" for the gels. The transition pressure of a gel is the pressure at which it will resist flow in the screen pack and represents the relative strength of the gel; the higher the transition pressure the stronger the gel. The following table shows the gel compositions and transition pressures as of 1 week after mixing the gels.

| Aluminum Citrate Solutions | | Gels | |
| --- | --- | --- | --- |
| Aluminum Weight % | Aluminum:Citrate Ratio | Aluminum ppm | Transition Pressure, psi |
| 3.20 | 1.9:1 | 15 | 2.1 |
| 3.20 | 1.9:1 | 7.5 | 5.1 |
| 3.20 | 1.9:1 | 3.75 | 4.6 |
| 4.24 | 1.7:1 | 15 | 1.3 |
| 4.24 | 1.7:1 | 7.5 | 5.3 |
| 4.24 | 1.7:1 | 3.75 | 5.5 |
| 4.26 | 1.5:1 | 15 | 3.1 |
| 4.26 | 1.5:1 | 7.5 | 5.3 |
| 4.26 | 1.5:1 | 3.75 | 6.0 |

The data shows that gels with substantial strength will form when low levels of aluminum are added to the polymer solution as aluminum citrate. The best gels consistently formed when the aluminum concentrations ranged from 7.5 to 3.75 ppm, or when the polymer:aluminum ratios were 40:1 to 80:1. The gels mixed with the higher aluminum concentration of 15 ppm, with a polymer:aluminum ratio of 20:1, were slightly weaker. This is probably due to over crosslinking of the polymer by the aluminum, which results in the polymer constricting and taking up less space in solution; thus, the resultant gel is weaker. The data also shows that, as of one week after forming, the gels crosslinked with aluminum citrate mixed at aluminum:citrate ratios ranging from 1.9:1 to 1.5:1 are similar in strength.

EXAMPLE 5

The purpose of this example is to illustrate the use of dry aluminum citrate made from aluminum chlorohydrate in making gels, and to show the effect of aluminum:citrate molar ratios on gel reaction rates. In this experiment, the dried aluminum citrate products were added to water and dissolved to make solutions of 1000 ppm aluminum by weight. The dilute aluminum citrate solutions were added to solutions of 300 ppm partially hydrolyzed polyacrylamide in 0.5 percent KCl, as described in Example 4 above, to make gels. The resultant gels were tested for transition pressure at four time intervals after mixing, as in Example 4 above. The following table summarizes the experiment:

| Dry Aluminum Citrate | | Gel Aluminum ppm | Transition Pressure, psi | | | |
| --- | --- | --- | --- | --- | --- | --- |
| Aluminum Weight % | Aluminum:Citrate Ratio | | 24 Hours | 1 Week | 3 Weeks | 5 Weeks |
| 12.84 | 1.9:1 | 15 | 4.8 | 3.3 | 1.1 | 1.2 |
| 12.84 | 1.9:1 | 7.5 | 5.0 | 5.2 | 4.6 | 4.5 |
| 12.84 | 1.9:1 | 3.75 | 5.4 | 6.2 | 5.5 | 5.5 |
| 12.32 | 1.7:1 | 15 | 5.4 | 2.1 | 1.0 | 1.0 |
| 12.32 | 1.7:1 | 7.5 | 5.2 | 4.4 | 4.3 | 4.1 |
| 12.32 | 1.7:1 | 3.75 | 5.0 | 6.2 | 6.0 | 5.0 |
| 11.65 | 1.5:1 | 15 | 6.0 | 3.1 | 1.0 | 1.1 |
| 11.65 | 1.5:1 | 7.5 | 4.6 | 5.1 | 4.1 | 4.0 |
| 11.65 | 1.5:1 | 3.75 | 4.6 | 6.1 | 5.0 | 5.1 |

The results show that the gels reached final transition pressures on the order of 4.0 to 5.0 psi, and that the final strengths were essentially independent of the aluminum:citrate ratio in the range tested. Also, a polymer:aluminum ratio of about 20:1 is too low, as the gels tend to deteriorate over time after forming; this is consistent with the results of Example 4.

EXAMPLE 6

The purpose of this example is to show how dry aluminum citrate can be dry blended with a dry polymeric material to form a single dry combination product which can be used to form gels. In the lab, fifteen dry blends of aluminum citrate and partially hydrolyzed polyacrylamide were mixed. Five different aluminum citrate solids were used, varying in aluminum:citrate ratio from 1:1 to 1.9:1. Each aluminum citrate solid was used to mix three gels at three different polymer:aluminum ratios, 20:1, 40:1 and 80:1. The polyacrylamide was the same as that used in Examples 4 and 5. To mix a gel, a sufficient amount of dry blend to give a polymer concentration of 300 ppm was added directly to a solution of 0.5 percent KCl in water while stirring. The solution was allowed to stir overnight, then was stored until needed for quantitative testing. The gels were tested periodically for transition pressure as in Example 5. The data is shown in the following table.

| Aluminum: Citrate Ratio | Polymer: Aluminum Ratio | Gel Transition Pressure, psi | | | |
|---|---|---|---|---|---|
| | | 24 Hours | 1 Week | 3 Weeks | 5 Weeks |
| 1.9:1 | 20:1 | 6.2 | 8.3 | 8.1 | 7.3 |
| 1.9:1 | 40:1 | 6.0 | 8.7 | 9.4 | 10.0 |
| 1.9:1 | 80:1 | 5.3 | 8.3 | 9.5 | 9.5 |
| 1.7:1 | 20:1 | 3.5 | 5.0 | 5.7 | 6.0 |
| 1.7:1 | 40:1 | 6.3 | 8.0 | 9.0 | 11.0 |
| 1.7:1 | 80:1 | 4.0 | 9.0 | 10.3 | 10.0 |
| 1.5:1 | 20:1 | 4.0 | 7.2 | 7.3 | 6.2 |
| 1.5:1 | 40:1 | 4.2 | 7.8 | 9.0 | 8.3 |
| 1.5:1 | 80:1 | 1.0 | 7.8 | 9.3 | 9.6 |
| 1.3:1 | 20:1 | 3.0 | 7.3 | 6.5 | 6.6 |
| 1.3:1 | 40:1 | <1 | 8.9 | 9.3 | 8.6 |
| 1.3:1 | 80:1 | <1 | 10.4 | 9.4 | 9.4 |
| 1.1:1 | 20:1 | <1 | 8.0 | 7.4 | 7.3 |
| 1.1:1 | 40:1 | <1 | 11.4 | 10.7 | 11.0 |
| 1.1:1 | 80:1 | <1 | 10.7 | 11.8 | 12.3 |

The data shows that the dry formulations tested gave final transition pressures ranging from 6 to 12.3 psi, when the polymer concentration was 300 ppm. For most in-depth applications, this is an adequate range of gel strengths to work with. To decrease or increase the strength, respectively, the polymer concentration can be decreased or increased using a given aluminum citrate formulation and polymer:aluminum ratio. As the aluminum:citrate ratio decreases, the gel formation rate decreases, due to the chelating effect of the extra citrate relative to the aluminum. The aluminum:citrate ratio does not significantly affect the final gel strength, however. The best polymer:aluminum ratio to work with is in the range 40:1 to 80:1 and greater, which is consistent with the results of Examples 4 and 5.

EXAMPLE 7

The purpose of this example is to provide some baseline data on how long it takes to dry a liquid aluminum citrate material and the final product quality. 20,588 lbs of liquid aluminum citrate was dried on a double drum dryer in a large-scale pilot trial. The initial product was 34 percent solids. Dry product was produced at a rate of about 250 lbs/hour. Over a 28-hour period, 7000 lbs of dry product was produced. The final product contained about 5 percent moisture, 8 percent aluminum, 31 percent chloride and was water soluble. The pH of a 5 percent solution of the dried aluminum citrate was about 6.5. Trial gels with the redissolved dried aluminum citrate product were successful.

While particular embodiments of the invention have been described, it will be understood that the invention is not limited thereto, since many modifications can be made, and it is intended to include within the invention any such modifications as fall within the scope of the claims.

I claim:

1. An aluminum citrate preparation in dry form having at least about 1.1 percent chloride by weight and a molar ratio of aluminum to citrate of between about 0.5:1 and about 2.2:1, capable of forming a clear aqueous solution having a pH between about 5.0 and about 9.0 at a concentration of at least about 3.1 percent by weight aluminum.

2. The aluminum citrate preparation of claim 1 having an aluminum:chloride molar ratio of at least about 1:3.

3. The aluminum citrate preparation of claim 1 having at least about 7 percent aluminum by weight.

4. A clear aqueous aluminum citrate preparation made by solubilizing the dry aluminum citrate preparation of claim 1 in sufficient aqueous medium to form an aluminum citrate solution having at least about 3.1 weight percent aluminum.

5. A clear aqueous aluminum citrate solution having at least about 3.1 percent by weight aluminum, a pH between about 5.0 and about 9.0 and a molar ratio of aluminum to citrate at most about 2.2:1.

6. A method for the preparation of a solution comprising aluminum citrate complex comprising the following steps:

a. providing a first aqueous solution comprising an aluminum-chloride containing complex wherein the aluminum:chloride ratio is at least about 1:3;

b. mixing said first solution with a second solution comprising citric acid to form a composition having a molar ratio of aluminum:citrate at most about 2.2:1;

c. stirring said composition of step b. continuously at a rate sufficient to keep the resultant slurry in motion;

d. adjusting the pH of said composition to between about 5.0 and about 9.0 to obtain a clear solution.

7. The method of claim 6 wherein the pH adjustment of step d. is carried out with a concentrated basic hydroxide solution of the formula MOH, where M is an alkali metal or ammonium cation.

8. The method of claim 6 wherein said aluminum-chloride-containing complex is provided in the form of aluminum chlorohydrate solution having a molar ratio of aluminum:chloride of about 1:2, a concentration of up to about 50 percent by weight and an aluminum concentration of up to about 12.5 percent by weight.

9. The method of claim 6 wherein said aluminum-chloride-containing complex is provided in the form of a mixture of aluminum chlorohydrate and polyaluminum chloride solution, said polyaluminum chloride solution having an activity of between about 25 percent and about 34 percent by weight, and a molar ratio of aluminum:chloride of at least about 1:3 aluminum:chloride.

10. A process of making a dry aluminum citrate preparation comprising:

a. providing a first aqueous solution comprising an aluminum-chloride containing-complex wherein the aluminum:chloride ratio is at least about 1:3;

b. mixing said first solution with a second solution comprising citric acid to form a composition wherein the molar ratio of aluminum:citrate is at most about 2.2:1;

c. stirring said composition of step b. continuously at a rate sufficient to keep the resultant slurry in motion;

d. adjusting the pH of said composition to between about 5.0 and about 9.0 to obtain a clear solution;

e. drying said composition.

11. The process of claim 10 wherein said drying is carried out using drum drying means.

* * * * *